(12) United States Patent
Carey

(10) Patent No.: US 7,914,733 B2
(45) Date of Patent: Mar. 29, 2011

(54) PHOTOCATALYST, METHODS FOR DEODORIZING, AND METHODS FOR MAKING A DEODORIZER SYSTEM

(75) Inventor: William F. Carey, West Hartford, CT (US)

(73) Assignee: Northrock Distribution, Inc., Rocky Hill, CT (US)

( * ) Notice: Subject to any disclaimer, the term of this patent is extended or adjusted under 35 U.S.C. 154(b) by 460 days.

(21) Appl. No.: 11/828,549

(22) Filed: Jul. 26, 2007

(65) Prior Publication Data

US 2008/0050272 A1 Feb. 28, 2008

Related U.S. Application Data

(60) Provisional application No. 60/823,216, filed on Aug. 22, 2006.

(51) Int. Cl.
*A61L 9/00* (2006.01)
*A62B 7/08* (2006.01)
(52) U.S. Cl. .......... 422/5; 422/122; 422/120; 422/4
(58) Field of Classification Search .......... 422/122, 422/120, 5
See application file for complete search history.

(56) References Cited

U.S. PATENT DOCUMENTS

| | | | |
|---|---|---|---|
| 5,919,422 | A | 7/1999 | Yamanaka et al. |
| 6,093,676 | A | 7/2000 | Heller et al. |
| 6,531,100 | B1 * | 3/2003 | Ogata et al. ........... 422/177 |
| 6,884,752 | B2 | 4/2005 | Andrews |
| 2004/0058249 | A1 * | 3/2004 | Cai et al. ............ 429/248 |
| 2004/0224147 | A1 * | 11/2004 | Chou ................. 428/331 |
| 2005/0129591 | A1 | 6/2005 | Wei et al. |

FOREIGN PATENT DOCUMENTS

| | | |
|---|---|---|
| EP | 0836527 B1 | 4/1998 |
| EP | 0978690 A2 | 9/2000 |
| EP | 1437397 A1 | 7/2004 |
| WO | WO2005044446 A1 | 5/2005 |
| WO | WO2006111089 A1 | 10/2006 |

OTHER PUBLICATIONS

International Search Report; International Application No. PCT/US/2007/016829; International Filing Date Jul. 26, 2007; Date of Mailing Dec. 19, 2007 (6 pages).
Written Opinion; International Application No. PCT/US2007/016829; International Filing Date Jul. 26, 2007; Date of Mailing Dec. 17, 2007 (7 pages).

* cited by examiner

*Primary Examiner* — Sean E Conley
*Assistant Examiner* — Regina Yoo
(74) *Attorney, Agent, or Firm* — Cantor Colburn LLP

(57) ABSTRACT

Disclosed herein are deodorizer systems and methods for making and using the same. In one embodiment, a deodorizer system comprises: a mesh, nanoparticle titania coating on the mesh, and a frame disposed around a periphery of the mesh such that the mesh is configured to be in optical communication with sunlight and for receiving contaminated gas to be deodorized. The mesh has an open area of greater than or equal to about 35%, and has greater than or equal to 6,400 openings/in$^2$. In another embodiment, a deodorizer system comprises: a mesh disposed in a housing and for receiving contaminated gas to be deodorized, nanoparticle titania coating on the mesh, and a UV light source disposed to be in optical communication with the mesh. The mesh has an open area of greater than or equal to about 35%, and has greater than or equal to 6,400 openings/in$^2$.

22 Claims, 1 Drawing Sheet

US 7,914,733 B2

PHOTOCATALYST, METHODS FOR DEODORIZING, AND METHODS FOR MAKING A DEODORIZER SYSTEM

CROSS-REFERENCE TO RELATED APPLICATIONS

This application claims the benefit of U.S. Patent Application Ser. No. 60/823,216, filed Aug. 22, 2006, which is incorporated by reference herein in its entirety.

BACKGROUND

This disclosure generally relates to deodorizers, and, more particularly, to deodorizer systems and methods for removing volatile organic compounds from enclosed environments.

Organic pollutants can be difficult to remove from enclosed environments. For example, smoke odors from a fire in a home; cigar and cigarette smoke odors in a home, vehicle, bar, or club; effluent odors in a bathroom; and mold or mildew odors in a carpet that has been wet; as well as many other odors. Treatment of organic pollutants is particularly problematic in relatively small or confined spaces. For example, within an automobile, organic pollutants contribute to passenger discomfort and windshield fogging. However, due to the automobile's size and geometry, the use of an active cleaning system is neither practical nor cost effective for the majority of automobiles.

There is a continuing need for effective, cost efficient, techniques and systems for deodorization of enclosed environments.

BRIEF SUMMARY

Disclosed herein are deodorizers, methods for deodorizing, and methods for making deodorizers.

In one embodiment, a deodorizer system comprises: a mesh, nanoparticle titania coating on the mesh, and a frame disposed around a periphery of the mesh such that the mesh is configured to be in optical communication with sunlight and for receiving contaminated gas to be deodorized. The mesh has an open area of greater than or equal to about 38%, and has greater than or equal to 10,000 openings per $in^2$.

In another embodiment, a deodorizer system comprises: a mesh disposed in a housing and for receiving contaminated gas to be deodorized, nanoparticle titania coating on the mesh, and a UV light source disposed to be in optical communication with the mesh. The mesh has an open area of greater than or equal to about 38%, and has greater than or equal to 10,000 openings per $in^2$.

In one embodiment, a vehicle comprises: an engine, a power train in operable connection with the engine and wheels, a steering mechanism in operable communication with the wheels, an interior, and a deodorizer system disposed in the interior and configured to be in optical communication with sunlight. The deodorizer system comprises a mesh, nanoparticle titania coating on the mesh, and a housing connected to the mesh, such that the mesh is configured to be in optical communication with sunlight.

In one embodiment, a method for deodorizing an enclosed area comprises: contacting a coated mesh of a deodorizer system with UV light, reacting organic material in air, and reducing a concentration of at least one organic material.

In one embodiment, a method for producing a deodorizer system comprises: contacting a mesh with a nanoparticle titania formula, passing the mesh between rollers to form a coating on the mesh, and drying the coating to form a coated mesh.

The above described and other features are exemplified by the following figures and detailed description.

BRIEF DESCRIPTION OF THE DRAWINGS

Refer now to the figures, which are exemplary, not limiting, and wherein like numbers are numbered alike.

DETAILED DESCRIPTION

Figure 1:
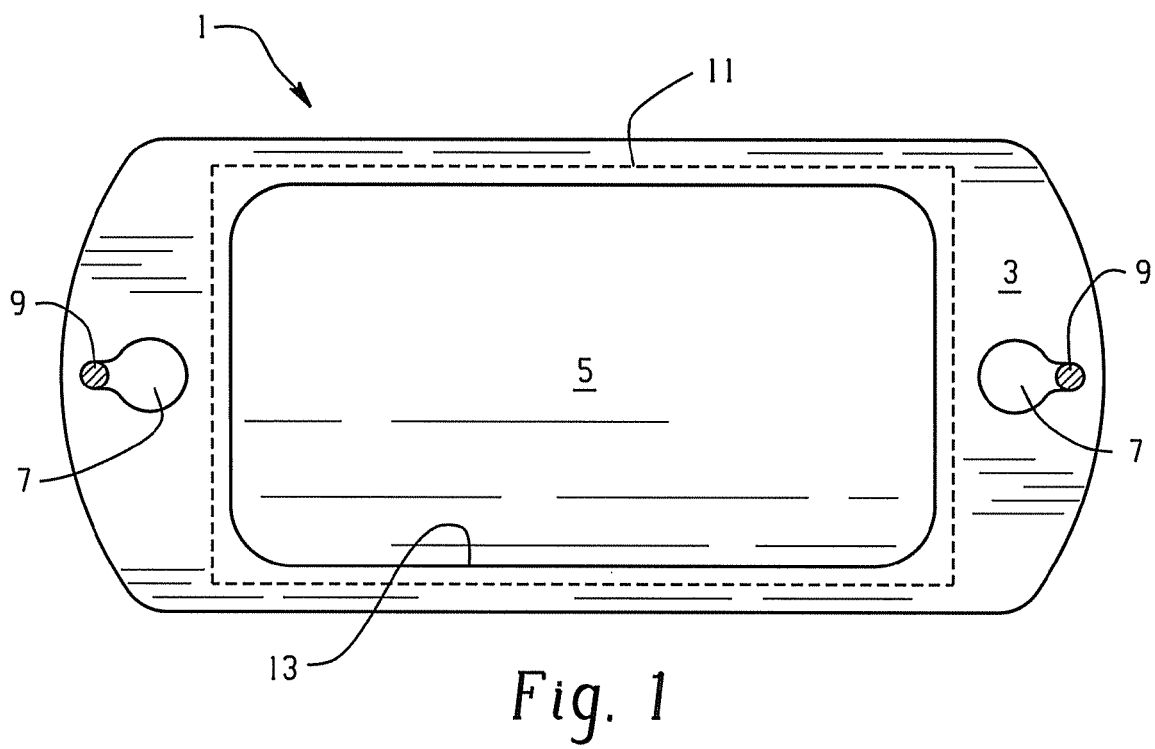
FIG. 1 is a frontal view of an embodiment of the deodorizer system.

Disclosed herein are photocatalysts, methods for deodorizing, and methods for making deodorizers. Deodorization of enclosed environments can be accomplished with natural convection currents; e.g., with no mechanical air moving device and with a natural power source such as the sun. Odor removal from enclosed spaces can be particularly difficult, depending upon the type of odor, length of order development, and type of space, as well as several other factors. For example, the system can be employed in the elimination of: mildew/mold smell from a carpeted room that had been flooded, smoke smell from a bar, smoke smell from a home that has had a fire, food smell (e.g., at a butcher, fish market, in a refrigerator, and so forth), cigar odor from a vehicle used for greater than or equal to a year by a cigar smoker, diaper odor, urine odor, pet odor; cleaning fluid odors; paint odors; petroleum odors; athletic equipment odors (e.g., shoe odor, soiled clothing smells); nursing home odors; funeral home odors; cadaver odors (e.g., in a corner's vehicle or laboratory); and chemical odors; as well as numerous other odors. This system can be used for deodorization of enclosed environments (such as a vehicle (e.g., recreational vehicle interior (including interiors of automobiles (internal combustion engine and diesel, trucks, cars, and so forth), boats), commercial vehicle interior (including buses, trucks, trains, ships, planes, and the like), military vehicle interiors (including submarines, tanks, ships, helicopters, planes, and so forth)), rooms (e.g., in an office, home, hospital, clinic, stores, factory, restroom), as well as combinations comprising at least one of the foregoing. Furthermore, the system is believed to have enhanced environmental resistance, thereby enabling it to exhibit an extended life when exposed to conditions such as salt air (e.g., near a body of salt water), humidity, and so forth.

The system can comprise a housing, support, and a photocatalyst. The photocatalyst comprises titanium oxide (also known as titania). The titania is located on the deodorant support. The housing, which is optional, imparts structural integrity to the deodorant support. For example, the system, which can use a sunlight as the power source, can comprise titania disposed on a mesh with a frame housing. In another embodiment, the system, which can use a powered ultraviolet (UV) emitting light source as the power source, can comprise titania located on a mesh and disposed in a cylinder in optical communication with the light source, and fluid communication with the surrounding environment, e.g., with a fan.

The photocatalyst comprises nanoparticle titania, which may be in the form of an aqueous solution(s) comprising nanoparticle titania. Desirably, the titania has an average particle size, as measured along a major axis (i.e., a longest axis), of less than or equal to 30 nanometers (nm), or, more particularly, less than or equal to about 20 nm, or, even more particularly, less than or equal to about 10 nm; e.g., an average particle size of about 5 nm to about 25 nm, or, specifically, about 8 nm to about 20 nm. The titania may be used in the form of particles or powder, or in the form of a sol. It may be used with wetting agent(s). For example a polyethylene oxide silane (e.g., in amount of 1 to 10 percent of the dry weight of the film former (titanium peroxide sol)); such as Dow Chemicals Silicone Q25211 super wetting agent (a polyethylene oxide silane). Optionally, an acrylic aliphatic urethane polymer can replace wholly or partially the titanium peroxide sol. Exemplary titania compositions are described in U.S. Pat. No. 6,884,752, to Andrews. One possible titania photocatalyst is commercially available from Prixmalite Industries, Inc., New York, N.Y., as TIOXOCLEAN® titanium dioxide solution. Not to be limited by theory, but for effectiveness, optical clarity, ease of application, durability, and/or adhesion, the titania can be nanoparticle size.

The titania can be disposed on the support that imparts structural integrity (e.g., a wall or other surface) and, desirably, that can enhance the available titania surface area available for deodorization. For example, the support can be a porous medium such as a mesh, (e.g., a woven or non-woven material such as cloth), perforated sheet, and so forth. The titania can be coated on and/or through (hereinafter "on") the cloth, that can be plastic and/or metal, can comprise materials such as metal (e.g., stainless steel (such as 304 stainless steel), carbon steel, brass, and so forth), non-metal (such as cotton, silk, plastic (e.g., polyester, polyvinyl chloride, polycarbonate, polyarylene ether, polystyrene, and so forth), canvas, as well as combinations comprising at least one of the foregoing. In some embodiments, the porous medium provides sufficient structural integrity to support the titania, provides sufficient surface area, and/or enables sufficient fluid flow therethrough to attain a desired deodorization rate. For example, the porous medium can have an open area of greater than or equal to about 35%.

The mesh design can comprise openings that facilitate the passage of gas (e.g., air) and sunlight, while adhering the coating. The mesh can have a number of openings, along one side, of greater than or equal to about 80 per inch (31.5 per centimeter (cm)), or, specifically, greater than or equal to about 100 per inch (39.4 per cm), or, more specifically, greater than or equal to about 110 per inch (43.3 per cm), and yet more specifically, great than or equal to about 120 per inch (47.2 per cm). Along the adjacent dimension (e.g., perpendicular direction), the number of openings can be greater than or equal to about 80 per inch (31.5 per cm), or, specifically, greater than or equal to about 100 per inch (39.4 per cm), or, more-specifically, greater than or equal to about 110 per inch (43.3 per cm), and yet more specifically, great than or equal to about 120 per inch (47.2 per cm). In other words, there can be about 100×110 openings per square inch (openings/in$^2$) (39.4×43.3 openings per square centimeter (openings/cm$^2$); i.e., 11,000 openings in a square inch (1,705 openings in a square centimeter). Desirably, there are greater than or equal to about 6,400 openings/in$^2$ (992 openings/cm$^2$), or, more specifically, greater than or equal to about 10,000 openings/in$^2$ (1,550 openings/cm$^2$), and even more specifically, greater than or equal to about 14,400 openings/in$^2$ (2,232 openings/cm$^2$).

The mesh thickness (e.g., wire/thread diameter) can be less than or equal to about 180 micrometers (μm), or, more specifically, less than or equal to about 150 μm, or, more specifically, less than or equal to about 120 μm, and, yet more specifically, less than or equal to about 90 μm. For example, in some embodiments, the diameter can be about 50 μm to about 120 μm. In other embodiments, the diameter can be about 120 μm to about 180 μm.

The square inch surface area of the wire cloth material is integral to its function by allowing millions of nanoparticles (microscopic) of the photocatalyst to adhere to the mesh. The surface area can be inversely calculated to the interior surface of the space, the concentrations of the coating, the number of coatings applied, and the opening size and thickness of the mesh. For example, to remove 95% of odors from the interior of a full size automobile (e.g., a station wagon), in less than or equal to about 24 hours, using sunlight as the UV source with the system mounted in the rear window, the surface area of the mesh is greater than or equal to 0.25 square feet (ft$^2$). For example, the mesh can have dimensions of about 10.5 inches by about 4 inches, with system dimensions of about 13 inches by about 5 inches. The screens can be made either smaller or larger depending on the size of the interior space and the type of contaminant or odor that is present within the space.

Depending upon the application, the coated mesh can be disposed in a housing having a two or three dimensional configuration, depending upon the particular application (e.g., to fit special windows, openings, and/or surfaces), the use of an on-board light source, sunlight, or another external light source. For instance, if the source of UV radiation is the sun, the housing should impart structural integrity to the system, and particularly to the coated mesh, while allowing optical communication between the coated mesh and the sunlight, and allowing fluid communication between the coated mesh and environment to be deodorized. When the source of UV radiation is an artificial light, the housing can provide structural integrity to the system, can allow fluid communication between the coated mesh and environment to be deodorized, and can facilitate optical communication between the UV source and the coated mesh. Where the coated mesh is disposed in the housing, an internal surface of the housing, or a portion thereof, can comprise a UV reflective material to enhance the rate of deodorization and more efficiently utilize the UV radiation produced by the UV source. Some possible housing designs include a frame (e.g., disposed around a periphery of the coated mesh), tube (e.g., a cylinder, or conical conduit), box, a clamp, and so forth.

Depending upon the application, the system, more particularly the housing, can also comprise an attachment element. The attachment element enables the system to be disposed in a desired location, e.g., attached to the interior surface of a rear window in an automobile, attached to hang from the rearview mirror in an automobile, and so forth. The attachment element can be clip(s), binder(s), suction cup(s), Velcro (i.e., a hook and loop system), rivet(s), screw(s), bolt(s), nail(s), adhesive, weld(s), snap fit(s), staple(s), and so forth, as well as combinations comprising at least one of the foregoing.

The particular size and material of the housing are dependent upon attaining sufficient structural integrity for the given application, attaining the desired speed of deodorization, the size of the interior space, and/or the odor(s) to be eliminated. For example, if the device will be used in an automobile interior (e.g., attached to a rear window), the housing can have a height of about 1 inch (in; 2.54 cm) to about 10 in (25.4 cm), or, specifically, about 2 in (5.1 cm) to about 6 in (15.2 cm). The length can be about 6 in (15.2 cm) to about 20 in (50.8 cm), or, specifically, about 10 in (25.4 cm) to about 15 in (38.1 cm). The thickness can be about 1/32 in (0.79 millimeters (mm)) to about 1/8 in (3.17 mm), e.g., about 1/16 in (1.59 mm) thick. In another embodiment, the device can be used in an automobile interior (e.g., hanging from a mirror or otherwise disposed), the housing can have a height of about 1 in (2.54 cm) to about 6 in (15.2 cm), or, specifically, about 2 in (5.1 cm) to about 4 in (10.2 cm). The length can be about 3 in (7.6 cm) to about 10 in (25.4 cm), or, specifically, about 4 in (10.2 cm) to about 8 in (20.3 cm).

In yet another embodiment, where the system will be employed in a bar, club (e.g., night club, club house, casino, or the like), morgue, and elsewhere that it is desirable to remove odors. The system can be designed as the screen for a window (e.g., the frame is the size of the window and the system replaces the window screen). Alternatively, or in addition, the system can comprise the housing (a polygon (e.g., a box) or a rounded container (e.g., a cylinder)) with the coated mesh, the UV source, and optionally a UV reflective material on inner surface(s), therein, and optionally an air mover capable of moving air through the housing. The housing can be designed in a decorative fashion to blend into the design of the area where it is used. When used in large areas the housing can have a size that is several feet or even yards in length and/or width.

The housing can be constructed from a material that is resistant to UV radiation as well as environmental conditions in the desired use location (e.g., thermal extremes and fluctuations, and/or moisture exposure). Possible materials include plastic (e.g., ABS plastic, polycarbonate, polyetherimide, polyvinyl chloride, polystyrene, and so forth), metal, and combinations comprising at least one of the foregoing. For example, the housing (e.g., frame, enclosure, etc.) can comprise high impact polystyrene capable of withstanding temperatures of 190° F. (88° C.) without warping or delaminating.

The power source can be an ultraviolet light source, such as solar power (sunlight), and/or artificial light (e.g., UVGI lamps, fluorescent light, UV emitting diodes, as well as any type of light source that emits UVA, UVB, and/or UVC). In other words, the system can function with no internal or on-board power source if sunlight is available and the housing is designed to allow optical communication between the photocatalyst and the sunlight.

Referring now to an exemplary illustration of the system in FIG. 1. The system 1 comprises the housing 3 disposed around the coated mesh 5. The housing has an opening 7 for receiving the attachment element 9 (e.g., suction cups). The attachment element 9 extends from an opposite side (not shown) of the frame 3, such that the system is capable of attachment to a glass surface such as the interior of the rear window of a car or truck.

Figure 2:
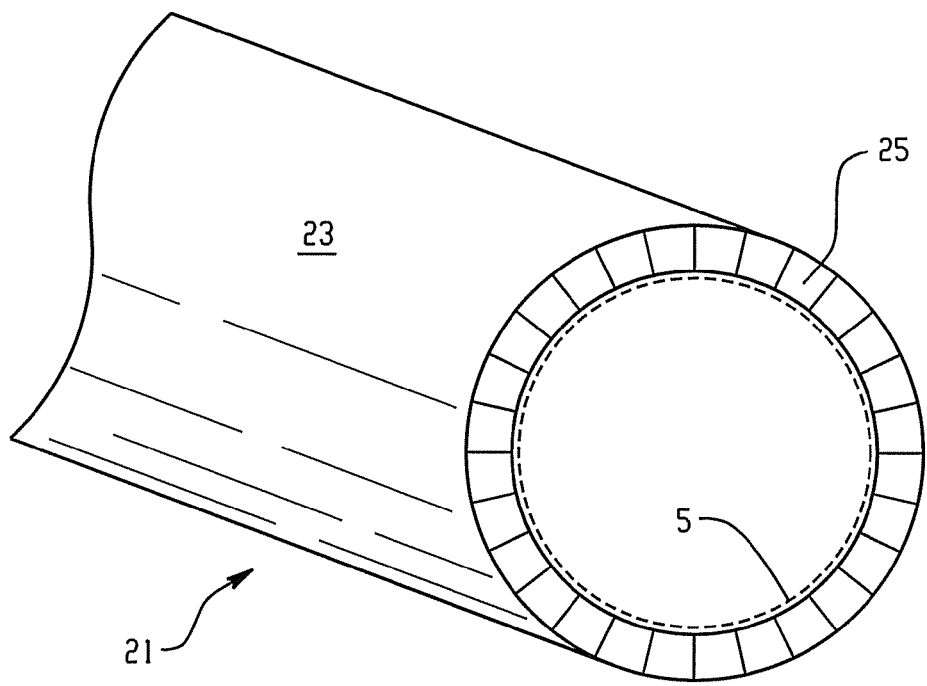
FIG. 2 is a partial, isometric view of another embodiment of the deodorizer system.

In FIG. 2, the deodorizer system 21 comprises a cylindrical housing 23, with a UV source 25 disposed in the housing, between the coated mesh 5 and the housing 23 such that air to be deodorized can pass through the housing 23 and contact the coated mesh 5.

The mesh can be coated before or after being disposed in the housing, depending upon the housing, to minimize handling of the coated mesh. Subsequently, the longevity of the product and the effect coincide with the surface coatings being of a specific thickness and covering. Sufficient coatings can be applied to the mesh to attain the desired thickness. In some embodiments, the thickness can be up to about 100 nanometers (nm), or, specifically, about 10 nm to about 60 nm, or, more specifically, about 20 nm to about 60 nm, or, yet more specifically, about 25 nm to about 35 nm. The coating can be applied in several coats. For example, it can be applied in 1 to about 10 coats, or, specifically, about 2 to about 8 coats, or, more specifically, about 3 to about 5 coats. The coatings can be applied in various fashions, such as painting, dipping, spraying, as well as combinations comprising at least one of the foregoing deposition processes. For example, the coating(s) can be applied with an electrostatic gun.

For two-dimensional applications, for example, the mesh can be disposed in the frame and then coated. Disposing the mesh in the frame can comprise forming the frame in two halves, disposing the mesh in one half of the frame, as illustrated in FIG. 1 (such that the mesh extends to a point 11 into the frame 3, past the inner periphery 13), and then securing the two sections together with a connector such as an adhesive, clamp(s), rivet(s), bolt(s), screw(s), snap fitting(s), heat, sonic welding, laminating, sealing (e.g., heat sealing), and/or other connection methods such as those described above-as-attachment elements. The frames can be formed by molding (casting, injection molding, and the like), stamping (e.g., from sheet materials), as well as other forming methods. The wire cloth is located between the two halves and is permanently suspended within the framework, forming the mesh frame assembly.

The frame can have an opening (e.g., keyhole opening) for receiving an attachment element, e.g., suction cup(s), and/or hanging hardware can be employed to fasten the attachment element(s). Alternatively and/or in addition, the frame and/or porous medium can comprise an attachment mechanism that is capable of retaining the system in a desired location.

The coated mesh can be produced by several methods. Before coating, the porous medium can be cleaned if it is desirable to remove manufacturer coatings and/or contaminants. A titania solution can then be applied to the porous medium. Although the solution can comprise up to and even exceeding about 10 volume percent (vol %) nanoparticle titania, a solution comprising about 0.25 vol % to about 6 vol % is often employed, or, specifically, about 0.5 vol % to about 3 vol %, or, more specifically, about 1 vol % to about 2 vol %, balance water and optional wetting agent(s). For example, the solution can comprise about 0.5 vol. % to about 4 vol %, or, more specifically, about 0.5 vol % to about 2.5 vol % TIOXOCLEAN® titanium dioxide solution.

The titania solution can be sprayed onto the porous medium and optionally the housing, e.g., as a cool (e.g., not heated, such as tap water at about 65 to about 75° F.) or warm (e.g., heated, e.g., water at about 80° F. to about 90° F. (alternatively, or in addition, the unheated tap water could be employed yet the air temperature increased to about 85° F. to about 90° F.)) vapor mist produced by compressed gas (e.g., air, nitrogen, or the like), or gas propelled aerosol can mixed with the titania solution (e.g., TIOXOCLEAN® titanium dioxide solution) and sprayed on both surfaces (2 dimensional surface) as well as the plastic frame. The titania solution can also be applied by immersing (dipping) the porous medium into the solution, either as an assembled unit (porous medium in the frame) or in sub-component parts before final assembly. Alternatively, or in addition, the porous medium can be pre-soaked in the solution while still in roll form, e.g., before the porous medium is cut to size for insertion into the housing.

The solution can then be actively (e.g., with blowers and/or heat (e.g., heated air, heating the porous medium, and so forth), or passively (allowed to air dry in ambient conditions) dried before applying an optional subsequent coating. Although a single coating can be used, it is preferred to apply several (e.g., 2, 3, or even 4) coatings of the solution to the mesh to attain a fully coated surface with good adhesion and sufficient reactivity.

An exemplary coating technique comprises spraying with clean compressed air (e.g., in 1 to 4 coating, or, more specifically, in two coatings). The first coating can be a light coating of $TiO_2$, on one or both sides of the screen, to pre-coat the screen, e.g., allowing the surface to dry in a gas stream. The gas stream can be any inert gas that does not adversely react with the coating, such as an air stream. The drying temperature can be room temperature or warmer, e.g., it can be a temperature of about 80° F. (27° C.) to about 90° F. (32° C.). The screen can then be coated, e.g., on both sides, with the second coat; again, drying with an air stream. The drying can be accomplished in various fashions such as by passing the coated screen material through a tunnel with warm air blowing therethrough, and/or by using a surface fan blowing warm air on the porous medium surface.

In another embodiment, the porous medium (e.g., screen) can be rolled after it is drawn into a submerged bath of the $TiO_2$ formula. The ribbon of screen can be drawn into and submerged in a bath of solution. As it rises out of the bath, it can be passed through rollers, spaced evenly above and below the ribbon material to form a squeegee effect, drawing the liquid and droplets off, forming a smooth, even coating of the material, and thereby uniformly coating the entire screen open surface. The same drying methods as above can be used. The screen can then optionally be passed through the bath process again before the material is sheared to the correct length for insertion into the screen frame. In yet another embodiment, the bottom roll can be immersed in a reservoir of the $TiO_2$ formula, creating a wick effect on the lower roller. This can allow the screen material to become saturated with the formula and allow the upper roller to wring the excess material off as it leaves the rollers. Exemplary roller materials include plastic and rubber rollers, such as neoprene, nitrile, and/or urethane. The nip (e.g., the space between the rollers) can be sufficient to receive the screen and allow the desired coating thickness. For example, the space can be less than or equal to about 50 micrometers.

Optionally, the $TiO_2$ formula can be heated, e.g., to a temperature of about 100° F. (38° C.) to about 140° F. (60° C.), prior to its application. Not to be limited by theory, it is believed that heating the formula enhances the ability for the water portion of the formula to evaporate, thereby enabling a significant decrease in curing time and allowing production to increase.

In other embodiments, water (e.g., cold water such as distilled water, at about 70° F.) along with the photocatalyst can be applied to a support as a vapor mist. For example, the water (distilled water) and photocatalyst can be sprayed from a vapor production nozzle (e.g., capable of producing a vapor having an average water particle diameter of in a less than or equal to about 25 micrometer (μm) range (or, more specifically, an about 7 μm to about 12 μm range). This can, for example, enable enhanced porous medium penetration, as well as photocatalyst dispersion and coatability on the porous medium. The photocatalyst is then desirably allowed to dry on the porous medium in ambient air. Optionally, the relative humidity can be maintained (under the given environmental temperature) at less than or equal to about 60%, e.g., about 15% to about 50%, to facilitate drying. The natural evaporation of the droplets leave sub-micrometer sized titania particles with improved adhesion, e.g., (not to be limited by theory) adhesion is believed to be on the molecular level. Additionally, multiple layering, namely a total of 3 layers of the solution, enabled complete porous medium (e.g., mesh) coating while not clogging the openings nor allowing the material to clump on the surface. Clumping would inhibit air and sunlight to freely pass through the porous medium and efficiently employ all dimensions of the porous medium.

The coated porous medium is very stable and can be handled after the coatings are applied. The coating is achieved on a molecular level achieved by electrical adhesion of the nanoparticle $TiO_2$ material to its surface. The coated mesh can be wound in lengths of about 100 feet to about 400 feet (30 meters to 150 meters) and optionally stored for later use. When used, the mesh can be sheared in lengths to fit the insert of the frame (which will be determined by the size of the frame being produced); e.g., a male insert is placed in the female frame such that the two halves can be attached together (e.g., can be sonic welded together) forming a permanent sealed bond.

During operation, air passes over and/or through the coated mesh. This movement can be via natural convection currents and/or with a device for moving gas over/through the coated mesh (such as a fan, pump, and so forth). As contaminated air (e.g., air comprising an odor), moves across and/or through the coated mesh, the photocatalyst, in the presence of UV light, destroys the odors. Not to be limited by theory, it is believed that the contaminated air is drawn into a hydroxyl radical field where oxidation occurs. Subsequently, volatile organic compounds (VOC's) and hydrocarbons are converted into carbon dioxide and water, thereby rendering odor causing substances inert; e.g., deodorized and deactivated.

The following examples are merely exemplary and are not intended to limit the generally broad scope thereof.

EXAMPLES

Example 1

Mesh Materials

Several types of mesh materials and configurations were tested, and several failed (e.g., exhibited a life of less than or equal to 15 weeks). Desirably, the system has a life of greater than or equal to about 20 weeks, or, specifically, greater than or equal to about 35 weeks, or, more specifically, greater than or equal to about 50 weeks, and, yet more specifically, greater than or equal to about 75 weeks.

TABLE 1

| No. | Mesh Material | Mesh Size (number of holes per square in) | Mesh diameter (in) | Open Area (%) | Life (weeks) |
|---|---|---|---|---|---|
| 1 | brass and bronze | 30 × 28 | 0.008 | 39 | 6 |
| 2 | brass, bronze, and stainless steel | 100 × 60 | 0.004 | 43.4 | 20 |
| 3 | brass, bronze, stainless steel, and galvanized | 120 × 108 | 0.0035 | 36.2 | 12 |
| 4 | stainless steel | 120 × 108 | 0.0026 | 47% | 54+ |
| 5 | stainless steel | 150 × 140 | 0.0026 | 50% | 32+ |

All samples were prepared by placing each Sample in a polyvinyl chloride frame half. The other frame half was joined to the first half with an adhesive to form an assembly. Three coatings of 2 vol % TIOXOCLEAN® titanium dioxide solution was then applied to the assembly by the cool air process; i.e., ambient air conditions, the use of tap water (about 70° C.), and a vapor mist application. The dried Samples were all tested by placing them in the rear window of a 4 door sedan under normal outside conditions. The doors of the vehicle remained closed during the entire duration with exception of entrance and egress.

Different types of odors were tested for neutralization. The interior of the automobile #1 had installed a series of air fresheners of differentiating types and sizes, the Sample 4, installed in a car in Rocky Hill, Conn., from January through July (about 0° F. to about 140° F.), neutralized all of the perfume odors. Automobile #2 was a smoker's car. Sample 4 was installed for a period of 3 days to remove all of the tobacco smell. This testing was repeated in numerous automobiles for a period of greater than 1 year, in Detroit, Mich., from April for over a year (in vehicle temperatures of about −10° F. to about 140° F.). After a year, Sample 4 was able to remove all odors as effectively as when originally used.

Also seen from Table 1, mesh materials that are oxidizable (e.g., brass, copper, and so forth) are less desirable than other mesh materials. Not to be limited by theory, when water based photocatalyst is applied to the mesh, the material of the mesh can oxidize, thereby reducing its life. Hence, oxidation resistant materials (e.g., stainless steel, and so forth) are used in some embodiments.

As can be seen from Table 1, the tests proved that different mesh sizes did not function well, with a stainless steel mesh having an open area of greater than 38%, more specifically, greater than or equal to about 40%, or, more particularly, greater than or equal to about 47% attaining unexpectedly improved results. Desirably the mesh has an open area of about 40% to about 55%, or, specifically, about 47% to about 50%. Airflow rates vary through the media and we found that the lower opening sizes, while allowing more air to pass through unimpeded, the surface area of titania was therefore less and the effect was decreased, thereby taking longer for the reaction to occur. Additionally, the mesh diameter can be less than or equal to about 0.0026 inches, for ease of manufacturing, reduced space requirements, enhanced heat transference and hence reduced stresses and affect on the housing.

It is also noted that other titania powder was tested. Tests included non-nanoparticle sized titania powder suspended in a whitewash solution as well as non-nanoparticle sized titania powder suspended in a resin solution; both were sticky. This titania did not last (i.e., deodorize) more than a few weeks, and off gassing of the bonder material masked a portion of the titania compound. Additionally, adhesion to the metal surface (metal mesh) was difficult if the surface was not made specifically cleaned, the screen was easily clogged with both of these solutions, and the applications were extremely limited. The water based nanoparticle solution was the better of the solutions tried, when working with very small opening screen or wire cloth material.

It is noted that with a larger particle size, the mesh will tend to have a build-up of material which will discolor the mesh surface and if re-wetted, may cause staining of the screen material a shade of yellow/green, thereby wasting material and reducing the effectiveness and life of the screen. The nano-particles (size of less than or equal to about 100 nm) are molecularly bonded to the surface wires of the screen and will tend not to come off unless washed by ammonia or acetone. The thicker surface area can be more easily removed.

The average concentration levels of cigarette smoke are 4-15 micrograms per meter cubed. This would be the concentration level that is tested for effects of second hand smoke. The odor screen can effectively remove this level of concentration in less than 2 hours (after the smoke is introduced) as long as the contamination is not re-introduced into the space. If the smoking contaminants (which typically do not constantly occur).

The present deodorizer system can be employed in enclosed spaces in various applications and configurations. The system can be operated with no internal power source, air source, or moving parts. For example, natural convection currents within the enclosed space accomplish the air movement and enable the complete deodorization of a full-size vehicle (e.g., a suburban comprising 15 μg/m of cigar smoke (such as from several months of smoking cigars in the vehicle over a period of several months)) in less than or equal to about 48 hours so long as the system is exposed to greater than or equal to about 6 hours of sunlight per 24 hour period, and with many contaminants and depending upon the light exposure, can enable complete deodorization even in less than or equal to about 24 hours. Since the deodorizer system (e.g., that employs the sunlight and/or with no air handlers) emits no sound or vibrations, the deodorizer system will not be affected by or affect the sound characteristics of the interior space (e.g., an automobile). The deodorizer system is silent in operation thereby causing no distraction to the occupants or the operator of the vehicle. The deodorizer system is lightweight and can adhere to any flat surface without marring or permanently defacing the surface to which it is attached. The device operates as long as UV light contacts the deodorizer system, and will last for an extended period of time (e.g., greater than or equal to one year) without any resurfacing of the coated mesh. The deodorizer system enables the neutralization of odors caused by pets (e.g., cat and dog), tobacco (e.g., cigarette and cigar), fuel, fiberglass, mold, mildew, cooking, bathroom effluents, as well as other offensive organic odors. Finally, the deodorizer system is both environmentally safe and stable.

It is further noted that the nano-particle titania can be applied to other substrates besides the mesh, such as on solid surfaces. Not to be limited by theory, it is believed that the coating will be less effective and efficient on a non-porous substrate. In addition to efficiency issues, the lifespan of the coating and its adhesions capabilities to the substrate may also be an issue. Additionally, since the coated system resists degradation (e.g., oxidation) by either salt spray or moisture in the atmosphere, it is also useful in extending the life of screening and other materials that are exposed to salt spray or humid environments.

It is understood that the deodorizer system removes odor(s) from the atmosphere in an area (e.g., within a vehicle, building, boat, etc.); it treats the airborne, ambient contaminants (e.g., odor(s)), not the source of the contaminants. If the deodorizer system is removed from the area, the odor(s) will return since the source of the contaminant(s) has not been removed, merely the airborne contaminant(s) themselves. In other words, if the carpet that emits pet odor, cigar odor, and so forth, remains, it will continue to emit the odor(s). It is the contaminant(s) in the atmosphere around the carpet that is treated, not the carpet. As a result, if the deodorizer is removed, the odor will return.

Ranges disclosed herein are inclusive and combinable (e.g., ranges of "up to about 25 wt %, or, more specifically, about 5 wt % to about 20 wt %", is inclusive of the endpoints and all intermediate values of the ranges of "about 5 wt % to about 25 wt %," etc). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. Furthermore, the terms "first," "second," and the like, herein do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context, (e.g., includes the degree of error associated with measurement of the particular quantity). The suffix "(s)" as used herein is intended to include both the singular and the plural of the term that it modifies, thereby including one or more of that term (e.g., the metal(s) includes one or more metals).

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A deodorizer system, comprising:
a mesh comprising an oxidation resistant material;
nanoparticle titania coating on the mesh; and
a frame disposed around a periphery of the mesh such that the mesh is configured to be in optical communication with a source of UV radiation and for receiving contaminated gas to be deodorized;
wherein the mesh has an open area of greater than or equal to about 47%, and has greater than or equal to 10,000 openings/in$^2$; and
wherein the coated mesh has a thickness of less than or equal to 180.1 µm and a life of greater than or equal to 20 weeks.

2. The deodorizer system of claim 1, wherein the mesh has greater than or equal to 11,000 openings per in$^2$.

3. The deodorizer system of claim 2, wherein the mesh has greater than or equal to 14,400 openings per in$^2$.

4. The deodorizer system of claim 1, wherein the mesh is stainless steel.

5. The deodorizer system of claim 1, wherein the titania has a particle size, as measured along a major axis, of less than or equal to 30 nm.

6. The deodorizer system of claim 5, wherein the particle size is less than or equal to 10 nm.

7. The deodorizer system of claim 1, wherein the source of UV radiation is sunlight.

8. The deodorizer system of claim 1, wherein the thickness is less than or equal to 120.06 µm.

9. The deodorizer system of claim 1, wherein the life is greater than or equal to 35 weeks.

10. A vehicle, comprising:
an engine;
a power train in operable connection with the engine and wheels;
a steering mechanism in operable communication with the wheels;
an interior; and
a deodorizer system disposed in the interior and configured to be in optical communication with sunlight, wherein the deodorizer system comprises
a mesh comprising an oxidation resistant material;
nanoparticle titania coating on the mesh; and
a housing connected to the mesh, such that the mesh is configured to be in optical communication with sunlight;
wherein the mesh has an open area of greater than or equal to about 47%, and has greater than or equal to 6,400 openings/in$^2$; and
wherein the coated mesh has a thickness of less than or equal to 180.1 µm and a life of greater than or equal to 20 weeks.

11. The vehicle of claim 10, further comprising photocatalyst disposed on at least a portion of an interior material, wherein the interior material is selected from the group consisting of carpet, seat covering, dashboard, roof covering, and rear window shelf material.

12. The vehicle of claim 10, wherein the housing is a frame disposed around a periphery of the mesh.

13. A deodorizer system, comprising:
a mesh disposed in a housing and for receiving contaminated gas to be deodorized, wherein the mesh comprises an oxidation resistant material;
nanoparticle titania coating on the mesh; and
a UV light source disposed to be in optical communication with the mesh;
wherein the mesh has an open area of greater than or equal to about 47%, and has greater than or equal to 10,000 openings/in$^2$; and
wherein the coated mesh has a thickness of less than or equal to 180.1 µm and a life of greater than or equal to 20 weeks.

14. A method for deodorizing an enclosed area, comprising:
contacting a coated mesh of a deodorizer system with UV light, wherein the deodorizer system comprises
the mesh coated with nanoparticle titania, wherein the coated mesh has a thickness of less than or equal to 180.1 µm and a life of greater than or equal to 20 weeks, and wherein the mesh comprises an oxidation resistant material; and
a housing connected to the mesh;
wherein the mesh has an open area of greater than or equal to about 47%, and has greater than or equal to 10,000 openings per in$^2$;
reacting organic material in air; and
reducing a concentration of the organic material.

15. A method for producing a deodorizer system, comprising:
contacting a mesh with a nanoparticle titania formula, wherein the mesh comprises an oxidation resistant material; and
drying the coating to form a coated mesh, wherein the coated mesh has a thickness of less than or equal to 180.1 µm and a life of greater than or equal to 20 weeks; and
wherein the mesh has an open area of greater than or equal to about 47%.

16. The method of claim 15, further comprising heating the titania formula to a temperature of about 38° C. to about 60° C. prior to contacting the mesh with the titania formula.

17. The method of claim 15, wherein the coating is dried at a temperature of about 27° C. to about 32° C.

18. The method of claim 15, further comprising
contacting the coated mesh with additional nanoparticle titania formula;
passing the coated mesh between rollers to form an additional coating on the mesh; and
drying the additional coating, wherein the coated mesh with the additional coating has a thickness of less than or equal to 180.1 µm.

19. The method of claim 18, further comprising heating the titania formula to a temperature of about 38° C. to about 60° C. prior to contacting the mesh with the titania formula.

20. The method of claim 15, further comprising disposing the coated mesh in between frame halves and sonic welding the frame halves together.

21. A deodorizer system, comprising:
a mesh comprising an oxidation resistant material;
nanoparticle titania coated directly on the mesh to form a coated mesh; and
a frame disposed around a periphery of the mesh such that the mesh is configured to be in optical communication with a source of UV radiation and for receiving contaminated gas to be deodorized;
wherein the mesh has an open area of greater than or equal to about 47%, and has greater than or equal to 10,000 openings/in$^2$; and
wherein the coated mesh has a life of greater than or equal to 20 weeks.

22. A deodorizer system, comprising:
a mesh comprising an oxidation resistant material;
nanoparticle titania coating on the mesh; and
wherein the mesh has an open area of greater than or equal to about 47%, and has greater than or equal to 10,000 openings/in$^2$; and
wherein the coated mesh has a life of greater than or equal to 35 weeks.

* * * * *